(12) United States Patent
Prudent et al.

(10) Patent No.: US 7,514,212 B2
(45) Date of Patent: Apr. 7, 2009

(54) NUCLEIC ACID AMPLIFICATION USING NON-STANDARD BASES

(75) Inventors: James R. Prudent, Madison, WI (US); Scott C. Johnson, Sun Prairie, WI (US); Michael J. Moser, Madison, WI (US); David J. Marshall, Madison, WI (US)

(73) Assignee: EraGen Biosciences, Inc., Madison, WI (US)

( * ) Notice: Subject to any disclaimer, the term of this patent is extended or adjusted under 35 U.S.C. 154(b) by 182 days.

(21) Appl. No.: 10/542,464

(22) PCT Filed: Jan. 17, 2004

(86) PCT No.: PCT/US2004/001397

§ 371 (c)(1), (2), (4) Date: Jun. 28, 2006

(87) PCT Pub. No.: WO2004/065550

PCT Pub. Date: Aug. 5, 2004

(65) Prior Publication Data

US 2007/0105099 A1    May 10, 2007

Related U.S. Application Data

(60) Provisional application No. 60/440,921, filed on Jan. 17, 2003.

(51) Int. Cl.
  *C12Q 1/68*     (2006.01)
  *C12P 19/34*    (2006.01)

(52) U.S. Cl. .......................................... 435/6; 435/91.2

(58) Field of Classification Search ...................... 435/6, 435/91.2
  See application file for complete search history.

(56) References Cited

U.S. PATENT DOCUMENTS

| | | | |
|---|---|---|---|
| 4,458,066 A | 7/1984 | Caruthers et al. | |
| 4,683,195 A | 7/1987 | Mullis et al. | |
| 4,683,202 A | 7/1987 | Mullis | |
| 4,800,159 A | 1/1989 | Mullis et al. | |
| 4,996,143 A | 2/1991 | Heller et al. | |
| 5,177,064 A | 1/1993 | Bodor | |
| 5,210,015 A | 5/1993 | Gelfand et al. | |
| 5,412,088 A | 5/1995 | Jones et al. | |
| 5,432,272 A | 7/1995 | Benner | |
| 5,470,974 A | 11/1995 | Summerton et al. | |
| 5,593,836 A * | 1/1997 | Niemiec et al. | 435/6 |
| 5,604,097 A | 2/1997 | Brenner | |
| 5,605,794 A | 2/1997 | Rust et al. | |
| 5,679,524 A | 10/1997 | Nikiforov et al. | |
| 5,681,702 A | 10/1997 | Collins et al. | |
| 5,705,621 A | 1/1998 | Ravikumar | |
| 5,736,330 A | 4/1998 | Fulton | |
| 5,763,169 A * | 6/1998 | Sandhu et al. | 435/6 |
| 5,843,669 A | 12/1998 | Kaiser et al. | |
| 5,846,717 A | 12/1998 | Brow et al. | |
| 5,856,092 A | 1/1999 | Dale et al. | |
| 5,928,869 A | 7/1999 | Nadeau et al. | |
| 5,958,784 A | 9/1999 | Benner | |
| 5,965,364 A | 10/1999 | Benner | |
| 6,001,983 A | 12/1999 | Benner | |
| 6,007,984 A | 12/1999 | Wang et al. | |
| 6,037,120 A | 3/2000 | Benner | |
| 6,046,807 A | 4/2000 | Chandler | |
| 6,054,270 A | 4/2000 | Southern | |
| 6,057,107 A | 5/2000 | Fulton | |
| 6,140,496 A | 10/2000 | Benner | |
| 6,232,462 B1 | 5/2001 | Collins et al. | |
| 6,294,336 B1 | 9/2001 | Boyce-Jacino et al. | |
| 6,444,798 B1 | 9/2002 | Benner | |
| 6,548,250 B1 | 4/2003 | Sorge | |
| 6,617,106 B1 | 9/2003 | Benner | |
| 6,627,456 B1 | 9/2003 | Benner | |
| 6,833,257 B2 | 12/2004 | Lee et al. | |
| 6,977,161 B2 | 12/2005 | Grenier et al. | |
| 7,422,850 B2 * | 9/2008 | Marshall et al. | 435/6 |
| 2002/0055104 A1 | 5/2002 | Michelotti | |

(Continued)

FOREIGN PATENT DOCUMENTS

EP    0 382 433 B1    8/1990

(Continued)

OTHER PUBLICATIONS

Biggins et al., "A continuous assay for DNA cleavage: The application of 'break lights' to enediynes, iron-dependent agents, and nucleases", *PNAS*, vol. 97, No. 25, Dec. 5, 2000 (pp. 13537-13542).

(Continued)

*Primary Examiner*—Kenneth R. Horlick
(74) *Attorney, Agent, or Firm*—Foley & Lardner LLP

(57) ABSTRACT

The present invention provides methods, kits and compositions for high fidelity nucleic acid amplification reactions of target nucleic acids such that specific amplification products that incorporate non-standard bases are produced. The amplification reactions can either be linear or exponential. In some embodiments, the fidelity of the amplification reaction is high enough such that a majority of the amplification products maintain non-standard bases at specific sites designated by the user after a specified number of amplification cycles. In some embodiments, the ratio of non-standard nucleoside triphosphates is greater than the amount of standard nucleoside triphosphates initially present in the reaction mixture.

22 Claims, 4 Drawing Sheets

U.S. PATENT DOCUMENTS

| | | | |
|---|---|---|---|
| 2002/0132221 | A1 | 9/2002 | Chee et al. |
| 2002/0150900 | A1 | 10/2002 | Marshall et al. |
| 2003/0194705 | A1 | 10/2003 | Schroth |
| 2004/0106108 | A1 | 6/2004 | Grenier et al. |
| 2006/0078936 | A1 | 4/2006 | Grenier et al. |

FOREIGN PATENT DOCUMENTS

| | | | |
|---|---|---|---|
| EP | 0 416 817 B1 | 3/1991 | |
| EP | 0 742 287 A2 | 11/1996 | |
| EP | 0 915 174 A1 | 5/1999 | |
| WO | WO 90/06042 A2 | 6/1990 | |
| WO | WO 92/11389 A1 | 7/1992 | |
| WO | WO 94/21820 A1 | 9/1994 | |
| WO | WO 96/31622 A1 | 10/1996 | |
| WO | WO 97/46711 A1 | 12/1997 | |
| WO | WO 98/14610 A2 | 4/1998 | |
| WO | WO 01/90417 A2 | 11/2001 | |
| WO | WO 0244195 A2 | * 6/2002 | |

OTHER PUBLICATIONS

Cobianchi et al., "Enzymes for Modifying and Labeling DNA and RNA", *Methods in Enzymology*, vol. 152, Copyright © 1987 by Academic Press, Inc., (pp. 94-110).

Hall et al., "Sensitive detection of DNA polymorphisms by the serial invasive signal amplification reaction", *PNAS*, vol. 97, No. 15, Jul. 18, 2000 (pp. 8272-8277).

Horlachet et al., "Recognition by viral and cellular DNA polymerases of nucleosides bearing bases with nonstandard hydrogen bonding patterns", *Proc. Natl. Acad. Sci.*, vol. 92, Jul. 1995 (pp. 6329-6333).

Jurczyk et al., "Synthesis of 2'-Deoxyisoguanosine 5'-Triphosphate and 2'-Deoxy-5-methylisocytidine 5'-Triphosphate", *Helvetica Chimica Acta*, vol. 82, 1999 (pp. 1005-1015).

Lutz, Michael J. et al., "Differential discrimination of DNA polymerases for variants of the non-standard nucleobase pair between xanthosine and 2,4-diaminopyrimidine, two components of an expanded genetic alphabet", *Nucleic Acids Research*, vol. 24, No. 7, 1996 (pp. 1308-1313).

Lutz, Stefan et al., "An in vitro screening technique for DNA polymerases that can incorporate modified nucleotides. Pseudothymidine as a substrate for thermostable polymerases", *Nucleic Acids Research*, vol. 27, No. 13, 1999 (pp. 2792-2798).

Moser et al., "Enzymatic repair of an expanded genetic information system", *Nucleic Acids Research*, vol. 31, No. 17, 2003 (pp. 5048-5053).

Newton et al., "The production of PCR products with 5' single-stranded tails using primers that incorporate novel phosphoramidite intermediates", *Nucleic Acids Research*, vol. 21, No. 5, 1993 (pp. 1155-1162).

PCT International Search Report, based on PCT International Application No. PCT/US04/01397, date of mailing of the International Search Report, Sep. 21, 2004 (1 pg.).

Piccirilli et al., "Enzymatic incorporation of a new base pair into DNA and RNA extends the genetic alphabet", Reprinted from *Nature*, vol. 343, No. 6253, Jan. 4, 1990 (pp. 33-37).

Randerath et al., "$_3$H and $_{32}$P Derivative Methods for Base Composition and Sequence Analysis of RNA", *Methods in Enzymology*, vol. 65, Copyright © 1980 by Academic Press, Inc., (pp. 638-681).

Sepiol et al., "Tautomerism of Isoguanosine and Solvent-Induced Keto-Enol Equilibrium", *Z. Naturforsch*, vol. 31, 1976 (pp. 361-370).

Switzer et al., "Enzymatic Recognition of the Base Pair between Isocytidine and Isoguanosine", *Biochemistry*, vol. 32, No. 39, 1993 (pp. 10489-10496).

Tor et al., "Site-Specific Enzymatic Incorporation of an Unnatural Base, $N^6$-(6-Aminohexyl)isoguanosine, into RNA", *J. Am. Chem. Soc.*, vol. 115, No. 11, 1993 (pp. 4461-4467).

Von Krosigk et al., "pH-Independent Triple Helix Formation by an Oligonucleotide Containing a Pyrazine Donor-Donor-Acceptor Base", *J. Am. Chem. Soc.*, vol. 117, No. 19, 1995 (pp. 5361-5362).

Walker et al., Isothermal in vitro amplification of DNA by a restriction enzyme/DNA polymerase system:, *Proc. Natl. Acad. Sci.*, vol. 89, Jan. 1992 (pp. 392-396).

Watanabe et al., "Two-Step Synthesis of 2,5'-Anhydronucleosides From Thymidine, 2'-Deoxyuridine, and 2'-Deoxy-5-fluorouridine", *Nucleic Acid Chemistry*, 1978 (pp. 273-277).

Zubay, "A Case for an Additional RNA Base Pair in Early Evolution", Reprint from: *The Roots of Modern Biochemistry*, © 1988 Walter de Gruyter & Co., Berlin, New York (4 pp.).

The Supplementary European Search Report based on Application No. EP 04 70 3107, date of completion of the Supplementary European Search Report, May 31, 2006 (2 pp.).

Switzer et al., "Enzymatic Recognition of the Base Pair between Isocytidine and Isoguanosine", *Biochemistry*, vol. 32, No. 39, Oct. 5, 1993 (pp. 10489-10496).

* cited by examiner

FIG. 1

JP185 (SEQ ID NO: 2)  
GTGGGTGCGTTCTTTCTTG

SCJ090 (SEQ ID NO: 5)

Dab CGACGCXGCCCGXCGGTCG FAM  
GTGGGTGCGTTCTTTCTTGCCGYCGGGCYGCGGACAGAGACGCAAGGAGAGA  
                                                   TCTCTCCTTGCGTCTCTGT

JP183 (SEQ ID NO: 3)            JP184 (SEQ ID NO: 1)

JP185 (SEQ ID NO:2)  
GTGGGTGCGTTCTTTCTTG

SCJ246 (SEQ ID NO:6)

Dab CGACGCXGCACGXCAGTCG FAM  
GTGGGTGCGTTCTTTCTTGCTGYCGTGCYGCGGACAGAGACGCAAGGAGAGA  
                                             TCTCTCCTTGCGTCTCTGT

SCJ245 (SEQ ID NO: 4)          JP184 (SEQ ID NO: 1)

FIG. 2
JP183/SCJ090
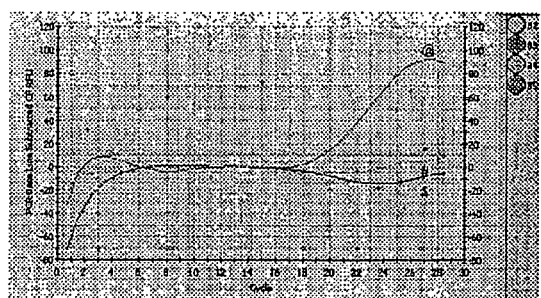
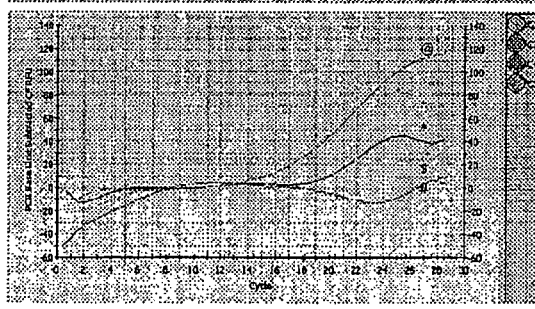
SCJ245/SCJ246
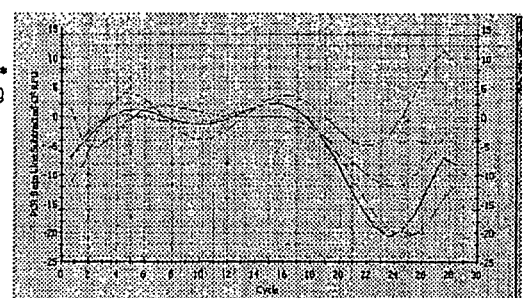
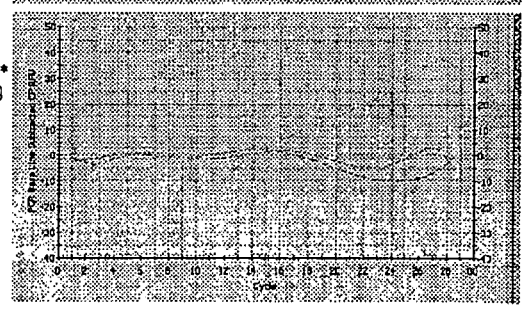

NUCLEIC ACID AMPLIFICATION USING NON-STANDARD BASES

CLAIM FOR PRIORITY

The present application claims priority to U.S. provisional patent application 60/440,921, the entire contents of which are hereby incorporated by reference.

FIELD OF THE INVENTION

The present invention relates to the amplification of a nucleic acid that contains one or more non-standard bases.

BACKGROUND

The storage of genetic information for all living systems is derived from the organizational string of just two base pairs (A:T and G:C). The simplicity of a two pair code is fascinating yet begs the question; are more than two possible? At least chemically, it has been shown that additional base pairs are possible.

The rule-based molecular recognition displayed by DNA makes it ideal throughout biotechnology, where molecules binding to molecules are needed for such applications as localizing DNA (see, e.g., Pease, A. C., et al., Proc. Natl. Acad. Sci. USA 91:5022-6 (1994)), assembling nanostructures (see, e.g., Collins, M. L., et al., Nucleic Acids Research 25:2979-2984 (1997)), building antibody-like molecules called "aptamers" (see, e.g., Prudent, J. R., et al., Science 264:1924-1927 (1994); and Hermann, T. and Patel, D. J., Science 287:820-825 (2000)) and performing tasks by which information in a molecular structure is recognized. Expanding DNA chemistry to include additional base pairs would enhance the capabilities of this powerful molecular recognition system. This in turn has lead chemists to develop new ways of increasing the number of DNA building blocks. The first experimental data suggesting that new base pairs could be used in replication, transcription and translation was demonstrated by Benner and colleagues using shuffled hydrogen bonding schemes, e.g., Piccirilli, J. A., et al., Nature 343:33-37 (1990) and Switzer, C. Y., et al., J. Am. Chem Soc. 111: 8322-8323 (1989). More recently, Romesberg and colleagues used the idea of hydrophobic interactions to create base pairs that did not rely on hydrogen bonding as disclosed in McMinn, D. L., et al., J. Am. Chem Soc. 121:11585-11586 (1999) and Tae, E. L., et al., J. Am. Chem. Soc. 123:7439-7440 (2001). With a specific mixture of two polymerases, the authors demonstrated incorporation followed by extension. Going one step further, Yokoyama and colleagues combined the concepts of shuffled hydrogen bonds and van der Waals interactions to develop a base pair that could be polymerized into RNA transcripts site specifically opposite the non-natural counterpart, e.g., Ohtsuki, T., et al., Proc. Natl. Acad. Sci. USA 98:4922-4925 (2001) and Mitsui, T., et al., J. Am. Chem. Soc. 125:5298-5307 (2003). More recently, it has been demonstrated that consecutive non-natural bases could be incorporated specifically opposite their non-natural counterparts and that other replication dependent enzymes can efficiently recognize a third base pair as disclosed in Moser, M. J., and Prudent, J. R., Nucleic Acids Research 31:5048-53 (2003). Yet the ability to place a third base pair into a commonly used replication system such as the polymerase chain reaction (PCR) has not been demonstrated.

SUMMARY

One embodiment described herein is a method of amplifying a nucleic acid that contains one or more non-standard bases. The method includes performing a nucleic acid amplification reaction on a sample having or suspected of having a template nucleic acid that comprises one or more non-standard bases. When the template nucleic acid is present in the sample during the amplification reaction, a nucleic acid amplification product that has specifically incorporated one or more non-standard bases is produced. In some embodiments, the fidelity of the amplification reaction is high enough such that a majority of the amplification products maintain non-standard bases at specific sites designated by the user after a specified number of amplification cycles. In some embodiments, the ratio of non-standard nucleoside triphosphates is greater than the amount of standard nucleoside triphosphates initially present in the reaction wherein the ratio is at least 1.5 to 1, 2 to 1, 3 to 1 or 4 to 1. In yet further embodiments, the fidelity of incorporation of non-standard bases into the nucleic acid amplification products is at least about 93%, 96% or more. In still further embodiments the polymerase in the nucleic acid amplification reaction can be thermostable and lack exonuclease activity, for example KlenTaq, TiTaq or combinations thereof. In some of the amplification reactions the unincorporated bases can be A, C, G, T or U, iC and iG. Additional embodiments of these methods can include detecting or measuring the nucleic acid amplification products, if present, and/or isolating or purifying the nucleic acid amplification products that are specific to the template nucleic acid.

Another embodiment provides the nucleic acid amplification product produced by the described methods. Still another embodiment provides a kit for amplifying a nucleic acid having one or more non-standard bases. The kit can include any or all of the following components: a polymerase enzyme, one or more non-standard nucleoside triphosphates, one or more standard nucleoside triphosphates, one or more primers, one or more target nucleic acids that comprise one or more non-standard bases, one or more oligonucleotide probes, and/or one or more molecular beacons.

A further embodiment provides a method for determining the initial amount of target nucleic acid having one or more non-standard bases, such as iso-C. The method includes cleaving the amplification products of a nucleic acid amplification reaction that contain labile non-standard bases and determining the initial target number or amount based on the cleavage amount or percentage. The initial target number or amount can then be determined, for example, by comparing the cleavage data to a standard curve, to a control reaction or by calculation taking into account the reaction conditions, such as cycle number and polymerase fidelity. This method takes advantage of the increased lability of non-standard bases, such as iso-C, under certain conditions, for example under acidic conditions, which can result in cleavage of the nucleic acid at the non-standard base position.

In another embodiment, the present invention provides a method of performing a nucleic acid amplification reaction comprising:

(a) performing a polymerase catalyzed nucleic acid amplification reaction on a sample having or suspected of having a target or template nucleic acid that is comprised of one or more non-standard bases, wherein the polymerase is capable of incorporating substantially only a non-standard base specific for the one or more non-standard bases on the target or template nucleic acid in the position complementary to the one or more non-standard bases on the target or template nucleic acid, wherein the polymerase is capable of adding further bases to the non-standard base specific for the one or more non-standard bases on the target or template nucleic acid, and further wherein the reaction is capable of reproducing the target or template nucleic acid when the target or template nucleic acid is present, In another embodiment, the present invention provides a method of performing a nucleic acid amplification reaction comprising:

(a) performing a polymerase catalyzed nucleic acid amplification reaction on a sample having or suspected of having a target or template nucleic acid that is comprised of one or more non-standard bases, wherein:

(i) the polymerase is capable of incorporating substantially only a non-standard base specific for the one or more non-standard bases on the target or template nucleic acid in the position complementary to the one or more non-standard bases on the target or template nucleic acid;

(ii) the polymerase is capable of adding further bases to the non-standard base specific for the one or more non-standard bases on the target or template nucleic acid;

(iii) the one or more non-standard bases of the target or template nucleic acid are selected from the group consisting of iso-C and iso-G; and (iv) the reaction is capable of reproducing the target or template nucleic acid when the target or template nucleic acid is present.

In the above embodiments the polymerase is capable of performing 20 or more rounds of amplification of the target or template nucleic acid without producing an appreciable and/or detectable amount of incorrect amplification products.

In any of the above embodiment the polymerase can lack exonuclease activity and can be KlenTaq. In any of the above embodiments, the target or template nucleic acid can be present in the sample and the target or template nucleic acid undergoes amplification. In these and other embodiments the non-standard bases can consist of iso-C and iso-G.

Any of the above embodiments can use a six base alphabet wherein the nucleotides available to the polymerase consist of A, C, G, U or T, iso-C and iso-G. In these and additional embodiments, the methods can further comprise detecting whether any amplification of the target or template nucleic acid occurs in (a).

Any aspect of the above embodiments can be suitably used with any other described embodiment.

BRIEF DESCRIPTION OF THE DRAWINGS

FIG. 1 depicts the nucleic acid sequences used in Example 1.

FIG. 2 illustrates the results of real-time PCR amplification performed as described in Example 1 using various combinations of bases.

DETAILED DESCRIPTION

Figure 3:
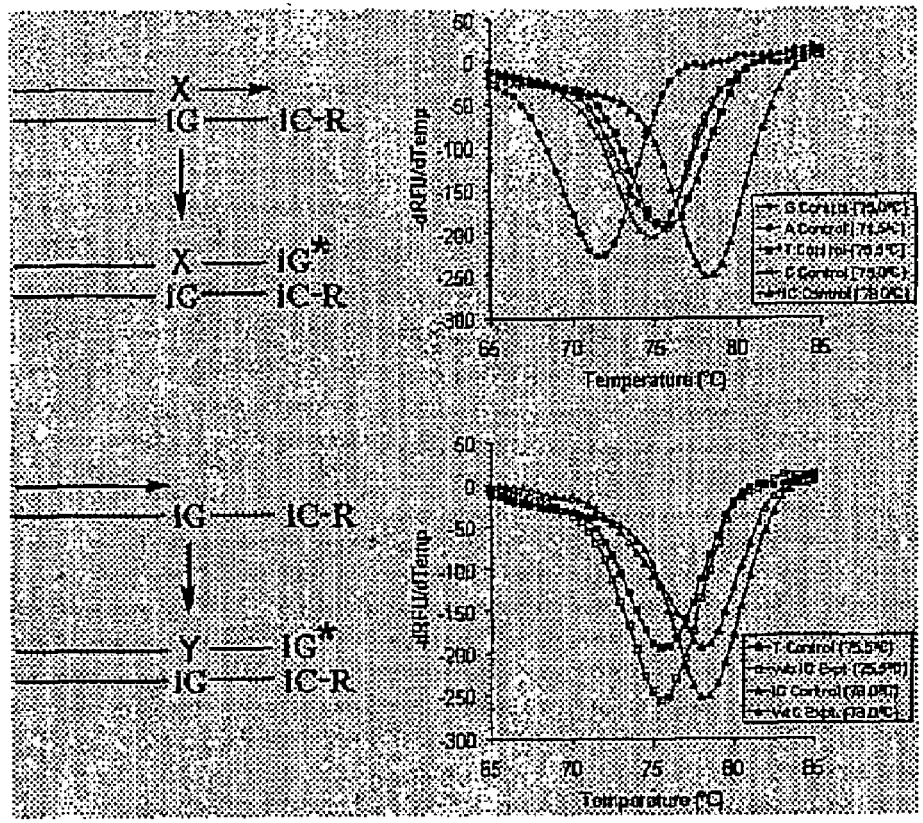
FIG. 3 shows primer extension and melt analysis described in Example 2. On the left, diagrams show where the 3'-end of primer hybridization to the template ended (after the iG in controls or before the iG for experimental. On the right, melt analysis of primer extension products where bases opposite iG were controlled (X=A,G,C,T,iC) or experimentally determined (Y). All reactions were treated with TiTaq, dG,dA,dT, dCTP, quencher-modified diGTP, and diCTP when designated. (R=tetrachloro-fluorescein and *=Dabcyl).

Described herein are methods, compositions and kits for performing a nucleic acid amplification reaction or synthesis that incorporate non-standard bases into the amplification products. Generally, the nucleic acid amplification reactions will have high fidelity and low misincorporation rates, particularly with respect to the specific incorporation of non-standard bases.

The polymerase chain reaction (PCR) is the most widely used method in molecular biology with applications that include: amplification, detection, quantitation, cloning, genotyping of genetic material, selection and screening of antibody and/or enzyme like nucleic acids, and taggant analysis, e.g., Clelland, C. T., et al., Nature 399, 533-4 (1999). Until now, PCR applications have been limited to placing non-natural base pairs into the priming regions and thus not requiring high-fidelity incorporation of the correct complements, e.g., Moser, M. J., et al., Clin. Chem. 49, 407-414 (2003). In order for the addition of a non-standard base pair between the priming sites of an exponential amplification system like PCR to be successful, the new bases should have a low rate of misincorporation, i.e., high fidelity incorporation of non-standard bases. The examples present data demonstrating that the non-standard bases and base pairs, such as the isoguanosine:isocytosine (iG:iC) base pair, can act as additional, specific base pairs for extension, replication and PCR amplification. The present methods, compositions and kits also contemplate that other specific, non-standard bases and base pairs, including specific base pairs, can be used. Using primer extension melt analysis, the experiments described herein show that the major percentage of incorporated nucleotide opposite iG is iC when provided with all six triphosphates in equal molar amounts. High polymerase fidelity was also confirmed, resulting in maintenance of the iC:iG base pair following PCR using a method of acid cleavage partial sequencing. Finally, an iC:iG containing molecular beacon was constructed and used to demonstrate applicability. The additional base pair will be useful in numerous other applications such as "aptamer" production, multiplexed diagnostics and those described above that utilize nucleic acid amplification of the naturally occurring nucleic acids. Accordingly, the present methods, kits and compositions can be used in any nucleic acid amplification reaction with corresponding utility as described above and elsewhere herein.

Nucleic acid amplification, such as PCR, is a method for the enzymatic amplification of specific segments of nucleic acids. The nucleic acid amplification is based on repeated cycles of the following basic steps: denaturation of double-stranded nucleic acid, followed by oligonucleotide primer annealing to the nucleic acid template, and primer extension by a nucleic acid polymerase (Mullis et al. and Saiki et al. 1985; and U.S. Pat. Nos. 4,683,195, 4,683,202, and 4,800, 159). The oligonucleotide primers used in nucleic acid amplification are designed to anneal to opposite strands of the DNA, and are positioned so that the nucleic acid polymerase-catalyzed extension product of one primer can serve as the template strand for the other primer. The amplification process can result in the exponential increase of discrete nucleic acid fragments whose length is defined by the 5' ends of the oligonucleotide primers.

Generally, these steps are achieved in a thermal cycling reaction. A typical thermal cycling reaction used in DNA amplification has a temperature profile of thermal cycling that involves an initial ramp-up to a predetermined, target denaturation temperature high enough to separate the double-stranded target DNA into single strands. Generally, the target denaturation temperature of the thermal cycling reaction is approximately 91-97° C., such as 94-96° C., and the reaction is held at this temperature for a time period ranging between 20 seconds to two minutes. Then, the temperature of the reaction mixture is lowered to a target annealing temperature which allows the primers to anneal or hybridize to the single strands of DNA. Annealing temperatures can vary greatly depending upon the primers and target DNA used. Generally, annealing temperatures range from 50° C.-70° C. depending upon the application. Next, the temperature of the reaction mixture is raised to a target extension temperature to promote the synthesis of extension products. The extension temperature is generally held for approximately two minutes and occurs at a temperature range between the annealing and denaturing temperatures. This completes one cycle of the thermal cycling reaction. The next cycle then starts by raising the temperature of the reaction mixture to the denaturation temperature. Typically, the cycle is repeated 20 to 40 times to provide the desired quantity of DNA. As will be understood by the skilled artisan, the above description of the thermal cycling reaction is provided for illustration only, and accordingly, the temperatures, times and cycle number can vary depending upon the nature of the thermal cycling reaction and application.

Typically, nucleic acid amplification or extension involves mixing one or more target nucleic acids which can have different sequences with a "master mix" containing the reaction components for performing the amplification reaction and subjecting this reaction mixture to temperature conditions that allow for the amplification of the target nucleic acid. The reaction components in the master mix can include a buffer which regulates the pH of the reaction mixture, one or more of the natural nucleotides (corresponding to A, C, G, and T or U—often present in equal concentrations), that provide the energy and nucleosides necessary for the synthesis of nucleic acids, primers or primer pairs that bind to the template in order to facilitate the initiation of nucleic acid synthesis and a polymerase that adds the nucleotides to the complementary nucleic acid strand being synthesized.

Some embodiments of the present reaction provide high fidelity amplification of nucleic acids containing non-standard bases, even over a high number of amplification cycles. In some of these embodiments, the fidelity or correct incorporation of non-standard bases opposite their specific pair can be about 75% and may be as high as 96% or more. Accordingly, nucleic acid amplification can be performed for 5, 10, 15, 20, 25, 30, 35, 40 cycles or more and still produce appreciable amounts of the correct nucleic acid. Typically, at least a majority of the nucleic acids produced by the amplification reaction will have the target sequence or its complement, although successful reactions can be performed if less than a majority of the nucleic acids are target specific. Some embodiments also provide nucleic acid amplification reactions in which 55% or more of the nucleic acid amplification products will have the target sequence or its complement. As will be apparent to the skilled artisan, the percent of specific nucleic acid product will depend on a number of factors, such as fidelity of incorporation, reaction cycle number, and the like, and these parameters can be varied to provide the desired result or amount of specific amplification product. In some embodiments, once the target is amplified, the specific amplification products having the target sequence alone or with its complement, can be isolated or purified from non-specific amplification products that do not have the target sequence or its complement. Additional embodiments will also measure the amount of specific amplification products present during or after nucleic acid amplification. The amount of amplification products can be measured using any suitable method, such as using probes, separation techniques, including electrophoresis, chromatography, HPLC, or the like.

In one embodiment, the amount of nucleic acid extension specific for the target can be measured by acid cleavage of the nucleic acid strands that contain iso-C bases, for instance as described in the examples. In some embodiments, once the nucleic acid amplification reaction is complete the resulting amplification products will be subjected to acidic conditions. Suitable pH's for acidic cleavage can be determined by those skilled in the art and may include a pH of 4, 3, 2, 1 or less. The amount or percentage of cleaved amplification product can then be compared to the amount of non-cleaved product to determine the percentage of specific amplification product. Given this amount or percentage, the initial amount or number of target nucleic acid in the sample can be determined. Typically, the initial amount of target nucleic acid can be determined by comparing percentage of cleaved product against a standard curve or one or more control reactions that have known amount of initial target. As will be apparent to the skilled artisan, it will also be useful to know the number of amplification cycles performed on the reaction mixture. The initial amount of target nucleic acid can also be determined based on the fidelity of the amplification, cycle number and final amount or percentage of cleaved amplification products.

As generally understood by the skilled artisan, "nucleic acids" include polymeric molecules such as deoxyribonucleic acid (DNA), ribonucleic acid (RNA), peptide nucleic acid (PNA), or any sequence of what are commonly referred to as bases joined by a chemical backbone where the bases have the ability to form base pairs or hybridize with a complementary chemical structure. Suitable non-nucleotidic backbones include, for example, polyamide and polymorpholino backbones. The term "nucleic acids" includes oligonucleotide, nucleotide, or polynucleotide sequences, and fragments or portions thereof. The nucleic acid can be provided in any suitable form, e.g., isolated from natural sources, recombinantly produced, or artificially synthesized, can be single- or double-stranded, and can represent the sense or antisense strand.

Advantageously, it has been discovered that the fidelity of non-standard base incorporation can be increased by altering the ratio of non-standard bases to standard bases available for extension during the nucleic acid amplification. In some embodiments, the concentration or amount of one or more of the non-standard bases, such as iso-C, iso-G or both, is increased relative to the standard bases, which are generally present in equal amounts, in the reaction mixture. For example, the concentration or amount of one or more of the free and unincorporated non-standard, bases can be 50%, 100%, 200%, 300%, 400% or more of the concentration or amount of the free and unincorporated standard bases such that the ratio of non-standard to standard bases is 1.5:1, 2:1, 3:1, 4:1, 5:1, 10:1 or more. Increased ratios of free non-standard bases has been found to particularly advantageous when the amplification reaction mixture contains and incorporates natural T bases, which can be mnisincorporated opposite iso-G, which is believed to result from a minor tautomeric form of iG that forms a mispair with T. Accordingly, compositions that provide these ratios are also described. The ratio of non-standard bases can also be decreased relative to the standard bases if desired. Incorporation of non-standard bases means that the non-standard bases are added to the amplification product during extension of a primer, rather than being present in the initial primer sequence.

Also encompassed are the amplified nucleic acids and mixtures produced according to the described methods herein.

Two additional bases generating a third base pair have been implemented into the polymerase chain reaction. Enzyme fidelity for the third base pair is demonstrated using molecular thermodynamic melting, chemical cleavage, and molecular beacons. When amplifying as few as 15 targets containing multiple non-natural base pairs with 40 cycles of amplification, the results set forth in the examples confirm sequence conservation. The additional sequence space provided by three base pairs allows for the construction of molecular tools that achieve higher complexity and better discrimination than those possible with natural DNA or RNA alone. Accordingly, the present methods, kits and compositions can be used for nucleic acid amplifications having, three, four or more specific base pairs.

In some embodiments, the pH of the nucleic acid amplification reaction solution is increased relative to nucleic acid amplification reactions containing only standard bases. The typical pH of PCR reactions is 8.3. Accordingly, some of the present methods can be performed in solutions that have a pH that is 8.5 or greater. In some instances, the pH will be greater than 9, such as 9.1 that can be achieved with a BIS-TRIS-propane-HCl buffer. pH can be increased up to 9.5 effectively. As will be apparent to the skilled artisan, the pH of the reaction solution should not be so high as to interfere with the amplification or result in excess degradation of the components in the reaction solution. In some embodiments, buffers that have a minimized delta pKa/degree C., such as BIS-TRIS-propane can be used, to prevent an increase in acidity in the reaction solution during heating.

The present application demonstrates that more than the standard four nucleoside triphosphates can be used in PCR amplification. The resulting amplified products can contain internal non-natural base pairs at positions corresponding to non-natural bases of the initial templates or to templates derived from the amplification. The additional information incorporated into PCR products will have applications in diagnostics, enzymology, molecular tagging and other areas where additional non-natural information based residues may be helpful.

In some embodiments, a solid support, which may be a single solid support, such as a chip or wafer, or the interior or exterior surface of a tube, cone, or other article is employed. The solid support is fabricated from any suitable material to provide an optimal combination of such desired properties as stability, dimensions, shape, and surface smoothness. Preferred materials do not interfere with nucleic acid hybridization and are not subject to high amounts of non-specific binding of nucleic acids. Suitable materials include biological or non-biological, organic or inorganic materials. For example, the master array can be fabricated from any suitable plastic or polymer, silicon, glass, ceramic, or metal, and can be provided in the form of a solid, resin, gel, rigid film, or flexible membrane. Suitable polymers include, for example, polystyrene, poly(alkyl)methacrylate, poly(vinylbenzophenone), polycarbonate, polyethylene, polypropylene, polyamide, polyvinylidenefluoride, and the like. Preferred materials include polystyrene, glass, and silicon.

Other types of solid supports can be used. In some embodiments, the solid support is a particulate support. In these embodiments, oligonucleotide probes are coupled to particles. Typically, the particles form groups in which particles within each group have a particular characteristic, such as, for example, color, fluorescence frequency, density, size, or shape, which can be used to distinguish or separate those particles from particles of other groups. Preferably, the particles can be separated using techniques, such as, for example, flow cytometry.

As contemplated in the invention, the particles can be fabricated from virtually any insoluble or solid material. For example, the particles can be fabricated from silica gel, glass, nylon, resins, Sephadex™, Sepharose™, cellulose, magnetic material, a metal (e.g., steel, gold, silver, aluminum, copper, or an alloy) or metal-coated material, a plastic material (e.g., polyethylene, polypropylene, polyamide, polyester, polyvinylidenefluoride (PVDF)) and the like, and combinations thereof Examples of suitable micro-beads are described, for example, in U.S. Pat. Nos. 5,736,330, 6,046,807, and 6,057,107, all of which are incorporated herein by reference. Examples of suitable particles are available, for example, from Luminex Corp., Austin, Tex.

As another example, the support can be a group of individual support surfaces that are optionally coupled together. For example, the support can include individual optical fibers or other support members that are individually coupled to different oligonucleotide probes and then bound together to form a single article, such as a matrix.

Typically, the support (whether a single or particulate support) is capable of binding or otherwise holding an oligonucleotide probe to the surface of the support in a sufficiently stable manner to accomplish the purposes described herein. Such binding can include, for example, the formation of covalent, ionic, coordinative, hydrogen, or van der Waals bonds between the support and the oligonucleotide probes or attraction to a positively or negatively charged support. Oligonucleotides probes are attached to the solid support surface directly or via linkers. In one embodiment, oligonucleotide probes are directly attached to the support surface by providing or derivatizing, either the surface, the oligonucleotide, or both, with one or more reactive groups. For example, the surface of the Luminex™ particles can be modified with, for example, carboxylate, maleimide, or hydrazide functionalities or avidin and glass surfaces can be treated with, for example, silane or aldehyde (to form Schiff base aldehyde-amine couplings with DNA). In some embodiments, the support or a material disposed on the support (as, for example, a coating on the support) includes reactive functional groups that can couple with a reactive functional group on the probe oligonucleotides. As examples, the support can be functionalized (e.g., a metal or polymer surface that is reactively functionalized) or contain functionalities (e.g., a polymer with pending functional groups) to provide sites for coupling the oligonucleotide probes.

As an alternative, oligonucleotide probes can be retained on the surface by cross-linking of the oligonucleotide probes. Preferably, an oligonucleotide probe that is cross-linked includes a cross-linking portion and a probe portion, wherein the probe portion includes a sequence that hybridizes to the sequence of the target oligonucleotide.

As yet another alternative, the support can be partially or completely coated with a binding agent, such as streptavidin, antibody, antigen, enzyme, enzyme cofactor or inhibitor, hormone, or hormone receptor. The binding agent is typically a biological or synthetic molecule that has high affinity for another molecule or macromolecule, through covalent or non-covalent bonding. The oligonucleotide probe is coupled to a complement of the binding agent (e.g., biotin, antigen, antibody, enzyme cofactor or inhibitor, enzyme, hormone receptor, or hormone). The oligonucleotide probe is then brought in contact with the binding agent to hold the oligonucleotide probe on the support. Other known coupling techniques can be readily adapted and used in the systems and methods described herein.

The present methods, kits and compositions are suitable for all nucleic acid amplifications and where nucleic acids are used. In many commercial applications, DNA is involved in two contexts. In the first, DNA-like binding is used to perform tasks by which information in a molecular structure is recognized. In the second, DNA is the "analyte", the target of the analysis, present in the biological sample in unknown amounts, sometimes having unknown sequence. DNA of the second type can obstruct the performance of DNA of the first type. Therefore, a molecular system that behaves like natural DNA but does not cross react with natural DNA would be useful. Paradoxically, if the new system shares structural similarity to DNA like the one presented here, the rich enzymology and technology already developed for DNA can be further exploited.

Consequently, the ability to place additional base pairs into DNA has several possible applications. Urdea and colleagues were the first to demonstrate diagnostic utility using branched DNA technology. Another application would be for molecular coding, where numerous technologies use DNA. Coding can be implemented in diagnostics to probe reaction products to solid phases, e.g., Landegren, U., et al., Science 241:1077-1180 (1988); Oliphant, A, et al., Biotechniques Suppl, 56-58, 60-61 (2002); and Chen, J., et al., Genome Research 10:549-57 (2000), where objects are marked with identifiable DNA segments called taggants; and in DNA computing. Gibbons, A., et al., Curr. Opin. Biotechnology 8:103-6 (1997). All would benefit from having extra bases orthogonal to naturally occurring DNA. Yet another application is in the field of aptamers, single-stranded and highly folded DNA and RNA molecules that, like antibodies, can bind target molecules with high affinity and specificity. Typically, aptamers are selected from large libraries of chemically synthesized oligonucleotides after multiple rounds of target binding and PCR amplification, e.g., Ellington, A. D. and Szostak, J. W., Nature 346:818-822 (1990). Catalytically active aptamers have been isolated with rate enhancement and turnover activities. However, aptamers made of standard nucleic acids are somewhat limited in enzymatic capability and therefore modified nucleic acids have been explored. See, for example, Battersby, T. R., et al., J Am Chem Soc 121, 9781-9789 (1999); and Santoro, S. W., et al., J Am Chem Soc 122, 2433-9 (2000). To expand on this, the use of multiple functional groups may be possible. Traditionally a single functionality is attached to uracil. This may be due to enzymatic reasons where placing chemical substituents on additional bases leads to premature termination. By increasing the number of building blocks, chemical substituents could be spaced further apart, thus allowing the polymerases to better process full length sequences. Additionally, DNA has found its way into nanotechnology because it can form molecular switches, assemble into 3-dimensional memory elements, create high density molecular recognition bio-chips and assemble into defined structures. Because of the simple rules used to create intricate DNA architectures and the tools used to screen and manipulate more complex DNA nanostructures, DNA is an obvious addition to nanotechnology.

The high fidelity of iC/iG incorporation demonstrated here is well within the range required for the applications discussed since tagging sequences used to probe iC/iG containing products' should not cross react with misincorporated natural sequences and selection schemes should eliminate any unfit sequences. The data presented should generate interest in not only creating new technologies using additional base pairs, but also in creating new organisms that rely on high fidelity enzymatic incorporation and specific enzyme recognition. Additional work to better understand the conditions necessary to use expanded genetic alphabets may also allow us to better understand how nature's alphabet evolved.

In some of the present methods, the nucleic acid amplification can be set up to achieve linear amounts of amplification, as discussed in Stump et al., Nucleic Acids Research 27(23):4642 (1999), or exponential or exponential growth of amplification, as in the well-known PCR technique. The nucleic acid amplification reactions can also be multiplexed to amplify more than one target nucleic acid, all or some if which can contain non-standard bases.

In most embodiments, the present methods and kits should use polymerase enzymes that are capable of properly incorporating non-standard bases in a nucleic acid, and preferably incorporate non-standard bases with high specificity for the base to which the non-standard base best pairs. In some embodiments, the polymerase enzymes lack exonuclease activity. Examples of a suitable polymerase are the KlenTaq and TiTaq polymerases. Klentaq1™ is the commercial name for Klentaq-278 which is a DNA polymerase having substantially the same amino acid sequence of the *Thermus aquaticus* or *Thermus flavus* DNA polymerase, but lacking the N-terminal 280 amino acid residues of *Thermus aquaticus* DNA polymerase, or the N-terminal 279 amino acids of *Thermus flavus* DNA polymerase as discussed in U.S. Pat. No. 5,436,149. Klentaq-278 substantially lacks exonuclease activity. TiTaq or TITANIUM™ Taq is a nuclease-deficient, amino terminal truncated mutant of *Thermus aquaticus* DNA polymerase available from Clontech. In some embodiments, the polymerases are not Taq, Tfl and Tgo as these polymerases have demonstrated the ability to misincorporate bases opposite a non-standard base although these polymerases may be used if the reaction conditions are modified as described herein to increase the fidelity of non-standard base incorporation.

As used herein "non-standard" or "non-natural" bases, pairing schemes, and base pairs are not the naturally occurring A, C, G, T and U bases and the AT, AU and GC base pairs. Generally, these "non-standard" bases, pairing schemes have hydrogen bonding patterns different from those found in the naturally occurring base pairs. In some embodiments the present amplification kits and methods use non-standard bases that pair specifically with only one other non-standard base, preferentially with high specificity. Examples of non-standard bases and base pairs are discussed in U.S. Pat. Nos. 5,432,272; 6,001,983; 6,037,120 and 6,140,496. Specific examples of non-standard bases include iso-C (iC) and iso-G (iG) that pair together as iC:iG. Other examples of nonstandard bases are those derived to specifically recognize certain non-standard bases that act as their complements but do this with means other than hydrogen bonding patterns. These would include but are not limited to those that use hydrophobic interactions to create base pairs and do not rely on hydrogen bonding for specific base pairing recognition.

In a specific embodiment, the present methods involve performing a nucleic acid amplification on a target nucleic acid containing one or more non-standard bases using a six base genetic code, four standard nucleic acids or nucleotides A, C, G and T or U and two non-standard bases iC and iG, using the KlenTaq or TiTaq enzyme as the polymerase. In some of these embodiments the reaction will be a PCR reaction, and will be amplify the target nucleic acid for 20, 25, 30 or more amplification cycles.

Fidelity of a polymerase enzyme, and in particular high fidelity, is a term familiar to those skilled in the art and is used to describe the ability of the polymerase enzyme to accurately incorporate a nucleotide across from the corresponding complementary nucleotide, i.e. the higher the fidelity of the polymerase, the higher percentage of correct incorporation events of the specific corresponding nucleotide. In some embodiments of the present methods, the fidelity of the polymerase enzyme will be sufficiently high to allow for 15, 20, 25, 30, 35 or 40 cycles or more, resulting in the majority of sequences having the initial nucleotide sequence derived from the starting template, e.g. 5%, 4%, 3%, 2%, 1% per cycle. In some embodiments the non-standard base incorporated by the polymerase enzyme will be incorporated in the complementary position to another non-standard base and not one of the naturally occurring bases. In some embodiments, not only will the first non-standard base pair specifically with a second, different non-standard base but the converse will also be true, specifically the second non-standard base will pair specifically with the first non-standard base and not other non-standard bases. In some embodiments, the non-standard bases will not only pair as described above, but they also will be incorporated into a nucleic acid strand during nucleic acid amplification only in a specific base pairing manner, i.e. they will only be incorporated into the nucleic acid being extended by the polymerase opposite the compatible, appropriate non-standard base, i.e., iC is incorporated substantially only across from iG and vice versa. As disclosed herein, such fidelity of incorporation is not only base specific it is also polymerase specific. Additionally, the polymerase will also generally be able to not only incorporate the non-standard base but also be capable of continuing past the non-standard base adding additional bases onto the extension product in a template specific manner. In other words, the polymerase should be capable of elongating the nucleic acid past any incorporated non-standard base.

The non-standard bases can be used in conjunction with the naturally occurring purines, adenine (A) or guanine (G), or pyrimidines, cytosine (C), thymine (T) or uracil (U). In some embodiments then T will not be used in the reaction mixture and will instead be replaced with U. Use of KlenTaq enzyme is surprising and unexpected because the polymerase from which KlenTaq is modified does not appear to provide the fidelity of incorporation that the KlenTaq enzyme provides. In some embodiments, U can replace T because it has been discovered that the KlenTaq polymerase will occasionally place a T across from iG in the process of nucleic acid amplification under certain conditions. Thus, the non-standard iG:iC base pairs will be converted into A:T. Surprisingly, replacing T with U in the reaction helps to overcome this problem because the KlenTaq polymerase does not appear to place U across from an iG. Thus, specific and high fidelity nucleic acid amplification reactions using at least three base pairs has been made possible with the use of the naturally occurring bases A, C, G and U in conjunction with iC and iG.

The methods described herein can further involve performing the nucleic acid amplification reaction on a reaction mixture that is capable of undergoing nucleic acid amplification when one or more target nucleic acids are present. After the nucleic acid amplification is performed, the presence or absence of the target nucleic acid can be determined or its amount measured. In order to facilitate detection or quantitation of the nucleic acid products, one or more of the primers, bases or nucleic acids used in the amplification reaction can be labeled. Detection of amplification product can also be measured in real-time using beacon sequences which can be labeled, for example with a fluorescent moiety and or a quencher moiety, as disclosed in Tyagi et al., Nature Biotechnology 14:303(1996). The target nucleic acid can be provided or isolated from a sample having or suspected of having a specific nucleic acid sequence. Additionally, a specific target nucleic acid having a known sequence can be added to the reaction.

The amplification reaction mixture can contain all, or only some, of the components necessary to perform the nucleic acid amplification, which can be added in any appropriate order. Generally, the components required for the nucleic acid amplification include buffer, magnesium ion, nucleotides that can be incorporated into a nucleic acid, such as deoxyribonucleoside triphosphates, polymerase enzyme and one or more primers. One skilled in the art will recognize that a successful PCR reaction will not occur in the absence of a target nucleic acid although the presence of a target nucleic acid is not required to perform the present methods.

Similarly, the efficiency of any nucleic acid amplification can also be measured an/or compared against a control reaction. In this manner, the effectiveness of different nucleic acid polymerases can be measured.

The present methods can be performed under varying stringency conditions. Variables affecting stringency include, for example, temperature, salt concentration, probe/sample homology, nucleic acid length and wash conditions. Stringency is increased with a rise in hybridization temperature, all else being equal. Increased stringency provides reduced non-specific hybridization. i.e., less background noise. "High stringency conditions" and "moderate stringency conditions" for nucleic acid hybridizations are explained in Ausubel et al., Curr. Prot. Mol. Biol., 1998, Green Publishing Associates and Wiley Interscience, NY. Low stringency conditions can also be used. Of course, the artisan will appreciate that the stringency of the hybridization conditions can be varied as desired, in order to include or exclude varying degrees of complementation between nucleic acid strands, in order to achieve the desired scope of detection. Likewise the protein and nucleic acid can be interacted under varying conditions which either enhance or interfere with protein-nucleic acid interactions.

The present methods can be used in a variety of applications including molecular tagging, SELEX, a variety of diagnostic applications and for the production of nucleic acid based therapeutics such as siRNA. The methods can also be used to produce branched nucleic acids incorporating non-standard bases and aptamers.

In some embodiments, the non-standard base pairs will not include non-specific or "universal" or "generic" bases, such as bases that can bind to two or more, i.e., 3, 4, or all 5, naturally occurring bases in a relatively indiscriminate or non-preferential manner with or without equal affinities. The present nucleic acids can also contain and incorporate such universal bases. Examples of such non-specific or universal bases include 2'-deoxyinosine (inosine), 3-nitropyrrole 2'-deoxynucleoside (3-nitropyrrole) and those disclosed in U.S. Pat. Nos. 5,438,131 and 5,681,947. Generally, when the base is "universal" for only a subset of the natural bases, that subset will generally either be purines (adenine or guanine) or pyrimidines (cytosine, thymine or uracil). Examples of nucleotides that can be considered universal for purines are known as the "K" base (N6-methoxy-2,6-diaminopurine), as discussed in Bergstrom et al., Nucleic Acids Research 25:1935 (1997) and pyrimidines are known as the "P" base (6H,8H-3,4-dihydropyrimido[4,5-c][1,2]oxazin-7-one), as discussed in Bergstrom et al., supra, and U.S. Pat. No. 6,313,286. Other suitable universal nucleotides include 5-nitroindole (5-nitroindole 2'-deoxynucleoside), 4-nitroindole (4-nitroindole 2'-deoxynucleoside), 6-nitroindole (6-nitroindole 2'-deoxynucleoside) or 2'-deoxynebularine.

Labels are useful moieties that can allow for simplified detection of nucleic acids containing nonstandard bases and can be attached to any desired moiety, such as a nucleotide or nucleic acid. The labels can facilitate either the direct, proximal or indirect detection and/or probe of the amplified product. Additionally, two of the moieties can be part of a unitary structure such that only two oligonucleotide moieties are utilized in the amplification reaction. As used herein, a label that is directly detectable produces a signal which is capable of detection either directly or through its interaction with a substance such as a substrate (in the case of an enzyme), a light source (in the case of a fluorescent compound) or a photomultiplier tube (in the case of a radioactive or chemiluminescent compound).

Examples of preferred direct labels include radioisotopic labels, e.g., the use of oligonucleotides which have incorporated $^{32}$P, $^{35}$S, $^{125}$I, $^{3}$H, and $^{14}$C. One approach for direct labeling of oligonucleotides is the end-labeling approach whereby T4 polynucleotide kinase is used to introduce a label into the 5' terminus of the oligonucleotide (see, e.g., Richardson, C. C., The Enzymes, Vol XIV, Nucleic Acids Part A, Ed. Boyer, P. D., Acad. Press, p. 299 (1981)). Alternatively, terminal deoxynucleotidyl transferase can be utilized to add a series of supplied deoxyribonucleotides onto the 3' terminus of the oligonucleotide; single nucleotide labeling methods can also be used (see, e.g. Bollum, F. J. The Enzymes, Vol. X, Ed. Boyer, P. D. Acad. Press, (1974); Yousaf, S. I. et al., Gene 27:309 (1984); and Wahl, G. M. et al. Proc. Natl. Acad. Sci. USA 76:3683-3687 (1979). Labeled ddNTPs, e.g.,—$^{32}$P ddATP, can also be utilized.

A label that is indirectly detectable does not in and of itself provide a detectable signal, however, it can be used to identify an oligonucleotide to which the indirectly detectable label is attached. Biotin, antibodies, enzymes, ferritin, antigens, haptens, etc. when conjugated to a dNTP or ddNTP comprise examples of indirectly detectable labels. Preferred non-radioactive direct labels include fluorescein-11-dUTP (see Simmonds, A. C. et al Clin Chem 37:1527-1528 (1991), incorporated herein by reference) and digoxigenin-1 dUTP (see Muhlegger, K. et al. Nucleosides & Nucleotides 8, pp. 1161-1163 (1989), incorporated herein by reference) can be utilized as labels. Additionally, non-radioactively labeled oligonucleotides, such as hapten labeled oligonucleotides may be used (see, e.g., Adams, C. W., PCT Patent Appln. WO 91/19729). A detection scheme involving such hapten-labels includes utilization of antibodies to the hapten, the antibodies being labeled. Biotin is an especially preferred indirect label, whereby the detection of biotinylated nucleic acid molecules is accomplished using labeled or insolubilized avidin, streptavidin, anti-biotin antibodies, etc. Biotinylated molecules can also be readily separated from non-biotinylated molecules by contacting the molecules with insoluble or immobilized avidin.

In this regard, for example, biotin-11-dUTP can be utilized in lieu of dUTP or dTTP, or biotin-14-dATP in lieu of dATP (see generally, Langer, P. R et al., Proc. Natl. Acad. Sci. USA 78:6633-6637 (1981), which is incorporated herein by reference). Biotinylated phosphoramidites can also be used (Misiura, K. et al. Nucleic Acids Research 18:4345-4354 (1990), which is incorporated herein by reference). Such phosphoramidites allow for precise incorporation thereof at desired locations along the growing oligonucleotide moiety during the synthesis thereof.

Chemiluminescent substrates can also be used as the indirect label. Enzymes, such as horseradish peroxidase ("HRP"), alkaline phosphatase ("AP"), etc. which can be directly cross-linked to nucleic acids may be employed (see, Renz, M. and Kurz, C., Nucleic Acids Research 12:3435-3444 (1964), incorporated herein by reference). Luminal, a substrate for HRP, and substituted dioxetanes, substrates for AP, can be utilized as chemiluminescent substrates. Exemplary of the HRP labeling protocol is the ECL system available from Amersham (Arlington Heights, Ill., USA).

In lieu of direct or indirect labels, a proximity label may be employed. Such a label is a chemical moiety which produces a signal only in the presence of a second label which interacts with it. Typically, a first proximity label is used in combination with a corresponding second proximity label.

It will be understood to those skilled in the art that the present methods readily lends themselves to automation.

The present oligonucleotides, methods and kits can be carried out by made or performing any of the characteristics described herein, either alone or in various combination. Additionally, one skilled in the art will realize that the present invention also encompasses variations of the present oligonucleotides and methods that specifically exclude one or more of the characteristics described above. As used herein "a" or "an" means "one" or "one or more."

Also provided are kits for carrying out the methods described herein. In one embodiment, the kit is made up of instructions for carrying out any of the methods described herein. The instructions can be provided in any intelligible form through a tangible medium, such as printed on paper, computer readable media, or the like. The present kits can also comprise one or more reagents, buffers, hybridization media, nucleotides, standard nucleoside triphosphates, non-standard nucleoside triphosphates, nucleic acids, nucleic acid probes, primers, nucleotides, molecular weight markers, enzymes, solid supports, databases, computer programs and/or disposable lab equipment, such as multi-well plates, in order to readily facilitate implementation of the present methods. Enzymes that can be included in the present kits include DNA polymerases, and the like. Solid supports can include beads and the like whereas molecular weight markers can include conjugated markers, for example biotin and streptavidin or the like. The kit components can be packaged in the same or separate containers as desired. Examples of suitable kit components can be found in the description above and in the following examples.

EXAMPLES

Example 1

The present example demonstrates the use of PCR amplification of a nucleic acid containing non-standard bases. In the following examples, iC is denoted X and iG is denoted Y.

In the following examples, JP184 (5'-TCTCTCCT-TGCGTCTCTGT-3') (SEQ ID NO: 1) and JP185 (5'-GTGGGTGCGTTCTTTCTTG-3') (SEQ ID NO: 2) are the primers used in each reaction. JP183 (5'-GTGGGTGCGT-TCTTTCTTGCCGYCGGGCYGCGGACA-GAGACGCAAGGAGAGA-3') (SEQ ID NO: 3) and SCJ245 (5'-GTGGGTGCGTTCTTTCTTGCTGYCGTG-CYGCGGACAGAGACGCAAGGAGAGA-3') (SEQ ID NO: 4) are the targets. SCJ245 differs from JP183 in that it has two A:T base pairs replacing G:C base pairs in the region between the priming sites. SCJ090 (5'-CGACGCXGC-CCGXCGGTCG-3') (SEQ ID NO: 5) and SCJ246 (5'-CGACGCXGCACGXCAGT CG-3) (SEQ ID NO: 6) were the labeled molecular beacons used for real time detection of the correct product. The beacons work by creating a hairpin when not in the presence of a complementary sequence. When in a hairpin conformation the FAM signal is quenched. As the specific product is generated by PCR and the beacon is unfolded during the denaturation cycle the two species with hybridize to each other as shown in FIG. 1. In this form the FAM dye is distal of the quencher and fluorescent signal is generated. KlenTaq1™ polymerase was obtained from aB Peptides Inc., St. Louis, Mo.

Example 2

The reaction conditions for this Example are shown below and the results for this Example are shown in FIG. 2. First, the effects of substituting U for T in the amplification of a target which required incorporation of G, A, T, C, X and Y was tested. The JP183 target does not require T, but SCJ245 does. Accordingly, on the left is the JP183 amplicon with T in the upper panel and U in the lower. The reactions with T are as observed above. G, A, C, X and Y(@) generates a product which hybridizes to the beacon, but when T(*) is added signal is lost. However, in the lower panel when T is replaced by U the G, A, C, X and Y(@) and the G, A, U, C, X and Y(*) reactions both generate an amplicon which hybridizes to the beacon. This suggests U is not as readily mispaired with iG allowing for iC to be properly incorporated. The panels on the right side are the target with internal A:T base pairs. Therefore neither of the G, A, C, X and Y reactions gave signal as all 6 bases are require for product formation. This reaction needs T in the reaction to pair with A. The G, A, T, C, X and Y(*) as expected gave no signal due to misincorporation. However, the G, A, U, C, X and Y(*) reaction does, thus illustrating the ability of U to lessen the mispairing with the iG tautomer.

Example 3

Primer Extension and Melt Analysis—A 5'-labeled template DNA oligonucleotide (5'-TET-T-iC-CGT-iG-CCGTCTCCGTCGTCAGCCGTCA-3') (SEQ ID NO: 7) at 200 nM was combined with a 2-fold excess of each control (5'-TGACGGCTGACGACGGAGACGGGACG-3' (SEQ ID NO: 8), 5'-TGACGGCTGACGACGGAGACGGAACG-3' (SEQ ID NO: 9), 5'-TGACGGCTGACGACGGAGACGG-TACG-3' (SEQ ID NO: 18), 5'-TGACGGCTGACGACG-GAGACGGCACG-3' (SEQ ID NO: 10), 5'-TGACGGCT-GACGACGGAGACGG-iC-ACG-3' (SEQ ID NO: 11)), or experimental DNA oligonucleotide (5'-TGACGGCTGAC-GACGGAG-3' (SEQ ID NO: 12)). Extension reactions were conducted in a 10 µL reaction volume containing 10 mM bis-tris-propane-HCl pH 9.1, 40 mM potassium acetate, 2 mM magnesium chloride, 0.1 mg/ml bovine serum albumin, 25 µM deoxyribonucleoside triphosphates (G, A, T, C and iC), 10 µM deoxy-isoguanosine triphosphate-Dabcyl (iGTP-Dabcyl), and 1× TiTaq (Clontech, Palo Alto, Calif.). Extension was performed using the following profile: 30 seconds at 95° C., 30 seconds at 60° C., and 1 minute at 65° C. Reactions were terminated by the addition of EDTA at 10 mM. Thermal melt analysis from 60° C. to 90° C. was performed on the iCycler (BioRad, Hercules, Calif.) using the following profile: 30 seconds at 60° C., 60 cycles of 10 seconds at 60° C. with an increase of 0.5° C. each cycle.

Non-natural Base Incorporation and Melt Analysis. A primer extension system was constructed to determine the identity of bases incorporated opposite iG under a variety of conditions. Parameters evaluated included nucleoside concentrations, buffering conditions and polymerase. In this system a fluorescence-quencher-modified diGTP was incorporated on the opposite DNA strands from a fluorescein label. Thermal melt analysis following primer extension separates the two strands, yielding melting temperature (Tm) determination. Comparison of the product Tm to those of control constructs where the base identity is known identifies the string of nucleotide incorporated, most importantly the nucleotide across from the non-natural base. These experiments led us to the discovery that increasing the ratio of non-natural triphosphates to natural triphosphates and using TiTaq (a nuclease-deficient, amino-terminal truncated mutant of *Thermus aquaticus* DNA polymerase) significantly reduced misincorporation opposite iG. These experiments also confirmed previous reports showing that thymidine was the major nucleoside incorporated opposite the iG when iCTP is withheld from the reaction, supporting the iG:T tautomer theory (FIG. 3).

Example 4

Acid Cleavage Analysis—Primer extension was conducted by combining SCJ1244 (5'-Cy3-CCAATG-TACGGGGTAAACTCT-3') (SEQ ID NO: 13) at 300 nM with either SCJ1247 5'-GAAGTCCAGCAATCAGAAC-TATGGCGACTCTCTACCTCCTGCAGGC-CCTACCACTTCCCAATAGCTAAGAGTT-TACCCCGTACATTGG-3') (SEQ ID NO: 14) or SCJ1248 (5'-GAAGTCCAGCAATCAGAACTATGGC-GACTCTCTACCTCCTGC-iG-GGCCC-iC-ACCACTTC-CCAATAGCTAAGAGTTTACCCCGTACATTGG-3') (SEQ ID NO: 15) at 200 nM in a 25 µL reaction volume using the same buffer conditions listed previously except 25 µM natural deoxyribonucleoside triphosphates (G, A, T and C) and 50 µM non-natural deoxyribonucleoside triphosphates (iG and iC). Extension was performed using the following profile: 1 minute at 95° C., 10 seconds at 55° C., and 30 seconds at 72° C. PCR amplicons were generated using the DNA oligonucleotides SCJ1244 and SCJ1243 (5'-GAAGTCCAG-CAATCAGAACTATG-3') (SEQ ID NO: 16) as primers at 200 nM. Ten-fold serial dilutions of SCJ1247 and SCJ1248 were made and 2.5 µL was used in a 10 µL reaction mix as described for the extension. Reactions were cycled according to the following profile: 1 minute 95° C., 40 cycles of (10 seconds at 95° C., 10 seconds at 55° C., 30 seconds at 72° C.).

Acid cleavage of the extension products was performed by mixing equal volumes of the extension reaction with 100 mM glacial acetic acid. Reactions were incubated for 30 minutes at 95° C. Reaction vessels were opened and acid was allowed to evaporate at 95° C. Two volumes of 100 mM ammonium hydroxide were added and the reactions were incubated for 5 minutes at 95° C. Reaction vessels were opened and the base was allowed to evaporate at 95° C. Cleavage products were resuspended in formamide, heated for 1 minute at 95° C., and analyzed by 7 M urea 10% polyacrylamide gel electrophoresis and fluorescence imaging. Cleavage products were quantitated using ImageQuant software (Amersham, Piscataway, N.J.).

Figure 4A:
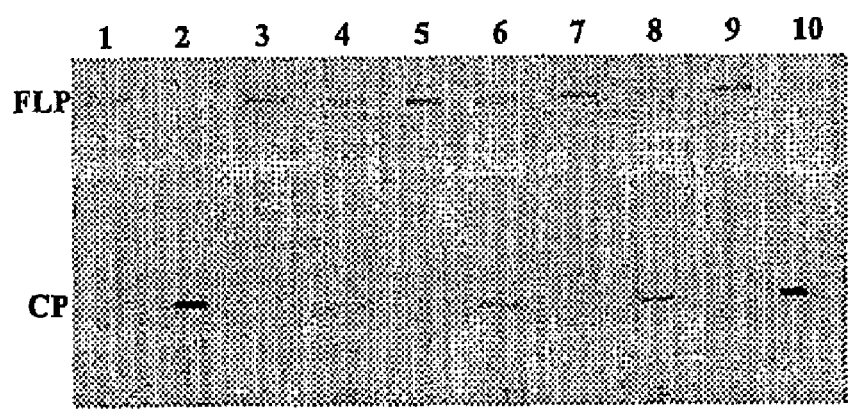
FIG. 4 depicts acid cleavage analysis described in Example 3. (A) Acid cleavage products using natural (odd lanes) and non-natural (even lanes) DNA targets. Reactions were resolved by PAGE and detected by fluorescent imaging. Lanes 1 and 2 were loaded with extension reactions that were initiated with $10^{10}$ copies of input target. Lanes (3-4, 5-6, 7-8 and 9-10) were loaded with PCR reactions initiated with $1.5 \times 10^1$ to $10^{10}$ input targets in 1000-fold increments and amplified with 40 cycles. Bands that appear in the scan that were used to determine percent cleaved are labeled (FLP=full length product and CP=cleavage product). (B) Cleavage analysis. Using a series of 10-fold dilutions of the non-natural template and 40 cycles of PCR, the percent of cleaved product was determined as above and plotted to input copy number.
Figure 4B:
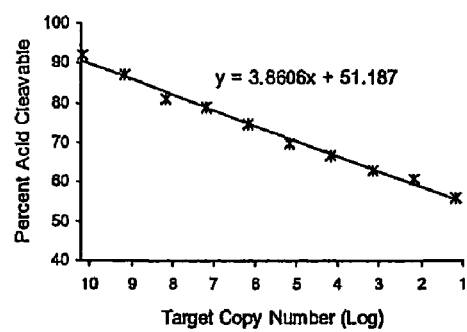

Confirmation of High Polymerase Fidelity. PCR and an acid cleavage partial sequencing method was next used to determine polymerase fidelity. It is well known that iC is more labile than naturally occurring bases under acid conditions, e.g., Voegel, J. J. and Benner, S. A., Helv. Chim. Acta 76:1863-1880 (1996). At low pH, nucleophilic substitution of the nucleobases followed by beta elimination leads to strand cleavage. Lindahl, T., Nature 362:709-15 (1993). At positions where the nucleobase is iC, this rate is faster than that of the naturally occurring bases. This information was used to monitor percentage of iC maintained in the final amplicon. Two 88 nt templates (1 and 2) were synthesized containing either two non-natural bases or none. The iC and iG in Template 1 were changed to T and A respectively in Template 2 since the primer extension experiments suggested that this would be the resolution of the iC:iG base pair if misincorporation were to occur. All reactions were cycled 40 times and included the six base nucleoside triphosphate mix, TiTaq and a forward primer fluorescently labeled with Cy3. Products were subjected to acidic and then basic conditions to cleave the strands primarily at positions containing the iC. Cleavage products were resolved using PAGE and percent cleaved was calculated by densitometry (FIG. 4). For reactions containing the non-natural bases, percent cleavage was plotted versus input template. The slope of the line (3.86) is the decrease in percent cleaved after each cycle which indicates that the fidelity of the iC:iG pair is ~96%.

Example 5

Molecular Beacon Analysis—PCR amplicons were generated as described in the acid cleavage analysis section except the DNA oligonucleotide primers used were SCJ1243 and (5'-CCAATGTACGGGGTAAACTCT-3') (SEQ ID NO: 19). The dual-labeled DNA oligonucleotide containing non-natural bases (5'-FAM-GTGCCGGT-iG-GGGCC-iC-GCAG-GAGGGGCAC-Dabcyl-3') (SEQ ID NO: 17) was used as a molecular beacon at 200 nM. DNA oligonucleotide templates for the PCR reactions were the same 10-fold serial dilutions of SCJ1247 and SCJ1248. Two and a half microliters of template from the dilution series was added to each reaction. The reactions were performed using an ABI 7700 instrument (Applied Biosystems, Foster City, Calif.) according to the following profile: 1 minute 95° C., 40 cycles of (10 seconds at 95° C., 20 seconds at 61° C., 1 minute at 65° C.). Real-time data was acquired at 61° C.

Figure 5:
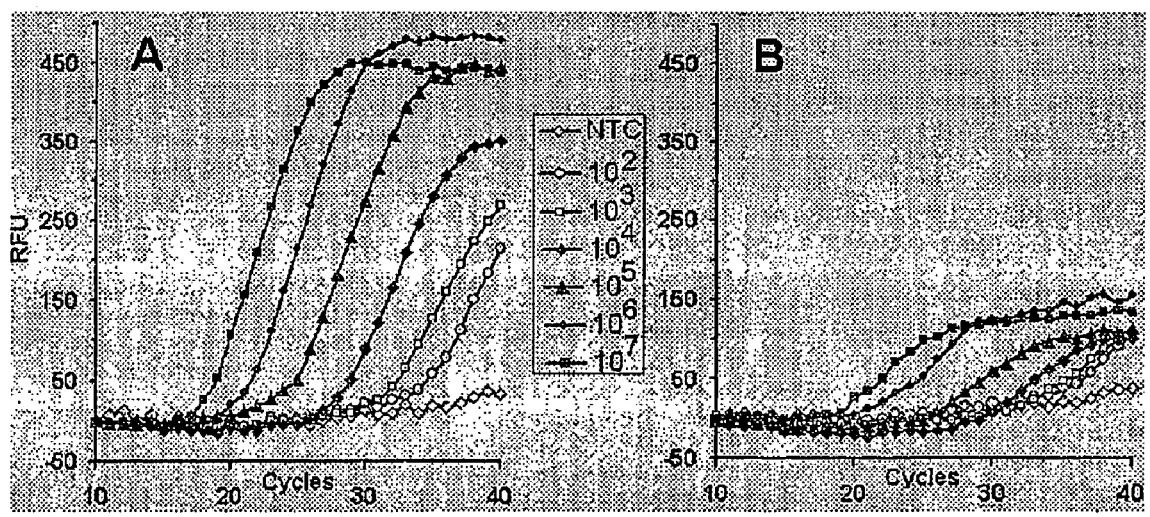
FIG. 5 shows molecular beacon analysis as described in Example 4. Amplification analysis using reactions containing Template 1(A) or Templates 2(B) and a molecular beacon specific for Template 1. Ten-fold dilutions of each target from $10^2$ to $10^7$ were constructed and added to the reaction series. The reactions were fluorescently monitored through 40 cycles of PCR.

Molecular Beacon Analysis of PCR Amplified Products. To demonstrate commercial applicability, a popular methodology termed "molecular beacons" was used to identify the buildup of iC:iG containing amplicons during PCR as disclosed by Tyagi, S. and Kramer, F. R., Nature Biotechnology 14:303-308 (1996). Molecular beacons are biosensors for the detection of specific DNA sequences. Specifically, molecular beacons are single stranded DNA structures that contain a pair of interacting fluorescent molecules that change fluorescent intensity once hybridized to their specific targets. Molecular beacons bind with high specificity and single base discrimination. These attributes appear ideal to discriminate between templates constructed from three base pairs and related templates constructed from two. In order to compare PCR efficiency, both templates were amplified using the same reaction mix which included the six base nucleoside triphosphate mix, TiTaq, a molecular beacon specific for the Template 1 (non-natural base containing target) and the identical primer set. The fluorescent output from the experiments was monitored and linear quantitation curves were constructed from the data (FIG. 5). PCR is an exponential amplification technology described by this formula; $N=N_o(e)^{(K*t)}$ where N=# of molecules, t=time (rounds of PCR), K=constant and thus a 10-fold increase in amplicon requires ~3.32 replication cycles for perfect doubling. Since the log of copy number to cycle threshold was plotted, a perfect doubling of each amplification round would provide a slope of ~0.301 [($2^{1/0.301}$) =10]. The slope of the line for Template 1 (Slope=−0.28±0.01) indicates that the amplification was not perfect and 3.6 cycles were required to yield a 10-fold increase, representing an efficiency of approximately 93% [Efficiency=$t_{perfect}/t_2=1/t_2=-m/\log(2)$ where m=slope]. Comparing peak fluorescent output from the two reactions sets (1 vs. 2), there appears to be a 3-fold increase when Template 1 was used, indicating that the beacon was specific for the correct target.

Discussion of Examples 2-4

The presented data demonstrate that an additional base pair can be implemented into the most widely used method in molecular biology, PCR, Earlier reports using the base pair (iC:iG), suggested that the iG would not be useful since thymidine would misincorporate opposite iG due to a minor tautomeric form of iG that forms a mispair with T. See, for example, Switzer, C. Y., et al., Biochemistry 32:10489-96 (1993). Many previous attempts using this base pair for PCR were unsuccessful and attributed to the tautomer hypothesis.

From the data reported here, it appears that the efficiency of the six base PCR system is high. Both the acid cleavage partial sequencing and the beacon experiments point to an overall incorporation efficiency of iC and iG to be ~96%±3%. These results compel us to believe that previous attempts fell short due to reasons other than tautomerization of the iG nucleotide. Other reasons seem more plausible and include: inappropriately low triphosphate concentrations: choice of polymerase; poor quality of iC/iG containing molecules; reaction pH's that were too destabilizing to iC at high cycling temperatures; and purification methods for templates and primers that were destabilizing to iC. The present methods can vary any combination or all of these parameters to increase nucleic acid amplification efficiency. The results indicate that a robust and reproducible system for expanded base pair chemistry using iC/iG has been produced.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group or genus, but also the main group or genus absent one or more of the group members or species. The present invention also envisages the explicit exclusion of one or more of any of the group members or species from the main group or genus in the claimed invention.

All references disclosed herein are specifically incorporated by reference thereto.

While preferred embodiments have been illustrated and described, it should be understood that changes and modifications can be made therein in accordance with ordinary skill in the art without departing from the invention in its broader aspects as defined herein.

The following references are also incorporated into the present application:

Held et al. Nucleic Acids Res. 30(17):3857 (2002);
Jurczyk et al., Helveta Chimica Acta 82:1005 (1999);
Lutz et al., Nucleic Acids Research 27(13):2792 (1999);
Lutz, et al., "Recognition of a Non-Standard Base Pair by Thermostable DNA Polymerases," Bioorganic & Medicinal Chemistry Letters 8:1149-52 (1998).
Michael J. Lutz, et al., "Differential Discrimination of DNA Polymerases for Variants of the Non-Standard Nucleobase Pair Between Xanthosine and 2,4-Diaminopyrimidine, Two Components of an Expanded Genetic Alphabet," Nucleic Acids Research 24 (7): 1308-13 (1996).
Christopher Roberts, et al., "Theoretical and Experimental Study of Isoguanine and Isocytosine: Base Pairing in an Expanded Genetic System," J. Am. Chem Soc. 119:4640-49 (1997).
Stephen J. Freeland, et al., "Early Fixation of an Optimal Genetic Code," Mol. Biol. Evol. 17 (4):511-18 (2000).
Eörs Szathmáry, "What is the Optimum Size for the Genetic Alphabet?," Proc. Natl. Acad. Sci. USA 89:2614-18 (April 1992).
Yiqin Wu, et al., "Efforts Toward Expansion of the Genetic Alphabet: Optimization of Interbase Hydrophobic Interactions," J. Am. Chem. Soc.122 (32):7621-32 (Aug. 16, 2000).
Dustin L. McMinn, et al., "Efforts Toward Expansion of the Genetic Alphabet: DNA Polymerase Recognition of a Highly Stable, Self-Pairing Hydrophobic Base," J. Am. Chem. Soc. 121:11585-86 (1999).
Eunju Lee Tae, et al., "Efforts Toward Expansion of the Genetic Alphabet: Replication of DNA with Three Base Pairs," J. Am. Chem. Soc. 123:7439-40 (2001).
Yoshinobu Kohara, et al., "DNA Probes on Beads Arrayed in a Capillary, 'Bead-array,' Exhibited High Hybridization Performance," Nucleic Acids Research 30(16):1-7 (2002).
Wolfgang Kusser, "Chemically Modified Nucleic Acid Aptamers for in vitro Selections: Evolving Evolution," Reviews in Molecular Biotechnology 74:27-38 (2000).
Lieven Stuyver, et al., "Line Probe Assay for Rapid Detection of Drug-Selected Mutations in the Human Immunodeficiency Virus Type 1 Reverse Transcriptase Gene," Antimicrobial Agents and Chemotherapy 41(2):284-91 (February 1997).
Frank B. Dean, et al., "Comprehensive Human Genome Amplification Using Multiple Displacement Amplification," Proc. Natl. Acad. Sci. USA 99(8):5261-66 (Apr. 16, 2002).
Michael C. Snabes, et al., "Preimplantation Single-Cell Analysis of Multiple Genetic Loci by Whole-Genome Amplification," Proc. Natl. Acad. Sci. USA 91:6181-85 (June 1994).

What is claimed is:

1. A method of amplifying a nucleic acid that contains one or more non-standard bases, comprising:

performing a nucleic acid amplification reaction on a sample having or suspected of having a template nucleic acid that comprises one or more non-standard bases selected from the group consisting of: iC and iG, wherein the ratio of unincorporated non-standard bases to unincorporated standard bases initially present in the nucleic acid amplification reaction is at least 1.5 to 1, and wherein when the template nucleic acid is present in the sample, a nucleic acid amplification product that has specifically incorporated one or more non-standard bases is produced.

2. The method of claim 1 wherein the fidelity of incorporation of non-standard bases into the nucleic acid amplification products is at least 93%.

3. The method of claim 2 wherein the fidelity of incorporation of non-standard bases into the nucleic acid amplification products is at least 96%.

4. The method of claim 1 wherein a polymerase in the nucleic acid amplification reaction is KlenTaq, TiTaq or combinations thereof.

5. The method of claim 1 wherein the unincorporated bases in the nucleic acid amplification reaction are selected from the group consisting of: A, C, G, T or U, iC and iG.

6. The method of claim 1 further comprising detecting or measuring the nucleic acid amplification product, if present.

7. The method of claim 6 wherein detecting or measuring the nucleic acid amplification product comprises capturing the nucleic acid amplification product to an oligonucleotide probe.

8. The method of claim 7 wherein the oligonucleotide probe is bound to a solid support.

9. The method in claim 7 where the oligonucleotide probe contains one or more non-standard bases.

10. The method of claim 1 wherein the nucleic acid amplification is a polymerase chain reaction.

11. The method of claim 1 wherein the nucleic acid amplification reaction is linear.

12. A method of amplifying a nucleic acid to generate a product that contains at least one non standard base, comprising:

performing a nucleic acid amplification reaction on a sample having or suspected of having a template nucleic acid, wherein when the template nucleic acid is present in the sample, a nucleic acid amplification product that has specifically incorporated one or more non-standard bases is produced, wherein the one or more non-standard bases are selected from the group consisting of: iC and iG, and wherein the ratio of unincorporated non-standard bases to unincorporated standard bases initially present in the nucleic acid amplification reaction is at least 1.5 to 1.

13. The method of claim 12 wherein the fidelity of incorporation of non-standard bases into the nucleic acid amplification products is at least 93%.

14. The method of claim 13 wherein the fidelity of incorporation of non-standard bases into the nucleic acid amplification products is at least 96%.

15. The method of claim 12 wherein a polymerase in the nucleic acid amplification reaction is KlenTaq, TiTaq or combinations thereof.

16. The method of claim 12 wherein the unincorporated bases in the nucleic acid amplification reaction are selected from the group consisting of: A, C, G, T or U, iC and iG.

17. The method of claim 12 further comprising detecting or measuring the nucleic acid amplification product, if present.

18. The method of claim 17 wherein detecting or measuring the nucleic acid amplification product comprises capturing the nucleic acid amplification product to an oligonucleotide probe.

19. The method of claim 18 wherein the oligonucleotide probe is bound to a solid support.

20. The method in claim 18 where the oligonucleotide probe contains one or more non- standard bases.

21. The method of claim 12 wherein the nucleic acid amplification is a polymerase chain reaction.

22. The method of claim 12 wherein the nucleic acid amplification reaction is linear.

* * * * *

UNITED STATES PATENT AND TRADEMARK OFFICE
CERTIFICATE OF CORRECTION

| | |
|---|---|
| PATENT NO. | : 7,514,212 B2 |
| APPLICATION NO. | : 10/542464 |
| DATED | : April 7, 2009 |
| INVENTOR(S) | : Prudent et al. |

Page 1 of 1

It is certified that error appears in the above-identified patent and that said Letters Patent is hereby corrected as shown below:

On the title page,

[*] Notice:   Subject to any disclaimer, the term of this patent is extended or adjusted under 35 USC 154(b) by 182 days Delete the phrase "by 182 days" and insert -- by 193 days --

Signed and Sealed this

Nineteenth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,514,212 B2 | Page 1 of 1 |
| APPLICATION NO. | : 10/542464 | |
| DATED | : April 7, 2009 | |
| INVENTOR(S) | : Prudent et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 445 days.

Signed and Sealed this

Ninth Day of November, 2010

David J. Kappos
*Director of the United States Patent and Trademark Office*

SEQUENCE LISTING

<160> NUMBER OF SEQ ID NOS: 19

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tctctccttg cgtctctgt                                                    19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtgggtgcgt tctttcttg                                                    19

<210> SEQ ID NO 3
<211> LENGTH: 52
<212> TYPE: DNA
<213> ORGANISM: Artificial Sequence
<220> FEATURE:
<223> OTHER INFORMATION: Description of Artificial Sequence: Synthetic

```
      oligonucleotide
<220> FEATURE:
<221> NAME/KEY: modified_base
<222> LOCATION: (23)
<223> OTHER INFORMATION: iG
<220> FEATURE:
<221> NAME/KEY: modified_base
<222> LOCATION: (29)
<223> OTHER INFORMATION: iG

<400> SEQUENCE: 3
gtgggtgcgt tctttcttgc cgncgggcng cggacagaga cgcaaggaga ga          52

<210> SEQ ID NO 4
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)
<223> OTHER INFORMATION: iG
<220> FEATURE:
<221> NAME/KEY: modified_base
<222> LOCATION: (29)
<223> OTHER INFORMATION: iG

<400> SEQUENCE: 4
gtgggtgcgt tctttcttgc tgncgtgcng cggacagaga cgcaaggaga ga          52

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: iC
<220> FEATURE:
<221> NAME/KEY: modified_base
<222> LOCATION: (13)
<223> OTHER INFORMATION: iC

<400> SEQUENCE: 5
cgacgcngcc cgncggtcg                                               19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: iC
<220> FEATURE:
<221> NAME/KEY: modified_base
<222> LOCATION: (13)
<223> OTHER INFORMATION: iC

<400> SEQUENCE: 6
cgacgcngca cgncagtcg                                               19

<210> SEQ ID NO 7
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: iC
<220> FEATURE:
<221> NAME/KEY: modified_base
<222> LOCATION: (6)
<223> OTHER INFORMATION: iG

<400> SEQUENCE: 7
tncgtnccgt ctccgtcgtc agccgtca                                          28

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tgacggctga cgacggagac gggacg                                            26

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tgacggctga cgacggagac ggaacg                                            26

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tgacggctga cgacggagac ggcacg                                            26

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)
<223> OTHER INFORMATION: iC

<400> SEQUENCE: 11
tgacggctga cgacggagac ggnacg                                            26

<210> SEQ ID NO 12
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 12
tgacggctga cgacggag                                                       18

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ccaatgtacg gggtaaactc t                                                   21

<210> SEQ ID NO 14
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gaagtccagc aatcagaact atggcgactc tctacctcct gcaggccta ccacttccca          60 atagctaaga gtttaccccg tacattgg                                            88

<210> SEQ ID NO 15
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)
<223> OTHER INFORMATION: iG
<220> FEATURE:
<221> NAME/KEY: modified_base
<222> LOCATION: (49)
<223> OTHER INFORMATION: iC

<400> SEQUENCE: 15
gaagtccagc aatcagaact atggcgactc tctacctcct gcnggcccna ccacttccca         60
atagctaaga gtttaccccg tacattgg                                            88

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gaagtccagc aatcagaact atg                                                 23

<210> SEQ ID NO 17
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: iG
<220> FEATURE:
<221> NAME/KEY: modified_base
<222> LOCATION: (15)
<223> OTHER INFORMATION: iC

<400> SEQUENCE: 17
gtgccggtng ggccngcagg aggggcac                                              28

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tgacggctga cgacggagac ggtacg                                                26

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ccaatgtacg gggtaaactc t                                                     21
```